(12) United States Patent
Shefer et al.

(10) Patent No.: US 6,887,493 B2
(45) Date of Patent: May 3, 2005

(54) MULTI COMPONENT CONTROLLED RELEASE SYSTEM FOR ORAL CARE, FOOD PRODUCTS, NUTRACEUTICAL, AND BEVERAGES

(76) Inventors: Adi Shefer, 14 Jason Dr., East Brunswick, NJ (US) 08816; Samuel David Shefer, 14 Jason Dr., East Brunswick, NJ (US) 08816

( * ) Notice: Subject to any disclaimer, the term of this patent is extended or adjusted under 35 U.S.C. 154(b) by 0 days.

(21) Appl. No.: 10/387,907

(22) Filed: Mar. 13, 2003

(65) Prior Publication Data

US 2003/0152629 A1 Aug. 14, 2003

Related U.S. Application Data

(63) Continuation-in-part of application No. 09/696,148, filed on Oct. 25, 2000, now Pat. No. 6,589,562.

(51) Int. Cl.$^7$ .............................. A61K 9/14; A61K 9/16; A61K 9/127
(52) U.S. Cl. ...................... 424/490; 424/450; 424/484; 424/489; 424/491; 424/492; 424/493
(58) Field of Search ................................ 424/400, 422, 424/434, 435, 439, 450, 484, 485, 489, 490, 491, 492, 493, 440

(56) References Cited

U.S. PATENT DOCUMENTS

| | | |
|---|---|---|
| 2,809,895 A | 10/1957 | Swisher |
| 3,922,354 A | 11/1975 | Galluzzi et al. |
| 3,949,094 A | 4/1976 | Johnson et al. |
| 3,962,463 A | 6/1976 | Witzel |
| 3,971,852 A * | 7/1976 | Brenner et al. ............. 426/103 |
| 3,976,794 A | 8/1976 | Johnson et al. |
| 4,217,368 A | 8/1980 | Witzel et al. |
| 4,230,687 A | 10/1980 | Sair et al. |
| 4,232,047 A | 11/1980 | Sair et al. |
| 4,259,355 A | 3/1981 | Marmo et al. |
| 4,420,534 A | 12/1983 | Matsui et al. |
| 4,532,145 A | 7/1985 | Saleeb et al. |
| 4,610,890 A | 9/1986 | Miller et al. |
| 4,689,235 A | 8/1987 | Barnes et al. |
| 4,707,367 A | 11/1987 | Miller et al. |
| 4,765,996 A | 8/1988 | Misaki et al. |
| 4,780,320 A | 10/1988 | Baker |
| 4,859,377 A | 8/1989 | Shasha et al. |
| 4,911,952 A | 3/1990 | Doane et al. |
| 4,929,447 A | 5/1990 | Yang |
| 4,971,797 A | 11/1990 | Cherukuri et al. |
| 5,009,900 A | 4/1991 | Levine et al. |
| 5,061,106 A | 10/1991 | Kent |
| 5,064,669 A | 11/1991 | Tan et al. |
| 5,077,051 A * | 12/1991 | Gallopo et al. ............. 424/435 |
| 5,087,461 A | 2/1992 | Levine et al. |
| 5,124,162 A | 6/1992 | Boskovic et al. |
| 5,183,690 A | 2/1993 | Carr et al. |
| 5,403,578 A | 4/1995 | Gordon |
| 5,418,010 A | 5/1995 | Janda et al. |
| 5,500,223 A | 3/1996 | Behan et al. |
| 5,506,353 A | 4/1996 | Subramaniam |
| 5,702,687 A * | 12/1997 | Miskewitz .................. 424/452 |
| 5,741,505 A | 4/1998 | Beyer et al. |
| 5,897,897 A | 4/1999 | Porzio et al. |
| 5,939,080 A | 8/1999 | Michael et al. |
| 5,955,502 A | 9/1999 | Hansen et al. |
| 5,972,404 A | 10/1999 | van Lengerich |
| 5,976,506 A | 11/1999 | Vernon |
| 5,989,535 A | 11/1999 | Nayak |
| 5,993,846 A | 11/1999 | Friedman et al. |
| 6,004,594 A | 12/1999 | van Lengerich |
| 6,007,795 A * | 12/1999 | Masterman et al. .......... 424/49 |
| 6,165,516 A | 12/2000 | Gudas et al. |
| 6,187,351 B1 | 2/2001 | Porzio et al. |

(Continued)

FOREIGN PATENT DOCUMENTS

| | | | | |
|---|---|---|---|---|
| EP | | 908174 A2 * | 4/1999 | ............ A61K/7/46 |
| WO | WO 93/00076 | | 1/1993 | |
| WO | WO 98/28398 | | * 7/1998 | |

OTHER PUBLICATIONS

Ronald J. Versic, Coacervation for Flavor Encapsulation, 1988, Chapter 14, pp. 126–131, American Chemical Society.

*Primary Examiner*—Thurman K. Page
*Assistant Examiner*—S. Tran
(74) *Attorney, Agent, or Firm*—Mathews, Collins, Shepherd & McKay, P.A.

(57) ABSTRACT

The present invention relates to an improved controlled release system that can encapsulate different flavors, sensory markers, and active ingredients, or combinations of flavors, sensory markers and various active ingredients and release multiple active ingredients in a consecutive manner, one after the other. The controlled delivery system of the present invention is substantially free-flowing powder formed of solid hydrophobic nanospheres that are encapsulated in a moisture sensitive microspheres. The flavors, and active ingredients encapsulated in the hydrophobic nanospheres, in the water sensitive microsphere, or in both the nano and the microsphere. The flavors and active ingredients encapsulated in the nanospheres can be the same or different from those encapsulated in the microspheres. The encapsulation of different flavors or active agents in the various components of the system, such as nanospheres and microspheres, provides flavor transition (change in flavor character) during the use of the products. The controlled release system of the present invention enhances the stability and bioavailability of wide range of flavors, sensory markers, and other active ingredients, prolong their residence time in the oral cavity, control their release characteristics, and prolong the sensation of flavors and other sensory markers in the mouth to provide long lasting organoleptic perception or long lasting mouthfeel. The invention further relates oral care, food products, and beverages comprising the controlled release system of the present invention.

30 Claims, 3 Drawing Sheets

U.S. PATENT DOCUMENTS

| | | |
|---|---|---|
| 6,245,366 B1 | 6/2001 | Popplewell et al. |
| 6,328,988 B1 | 12/2001 | Uhrich |
| 6,416,799 B1 | 7/2002 | Porzio et al. |
| 6,428,827 B1 | 8/2002 | Song et al. |
| 6,436,543 B1 | 8/2002 | Endo et al. |
| 6,440,449 B1 | 8/2002 | Hirschberg |
| 6,468,568 B1 | 10/2002 | Leusner et al. |
| 6,500,463 B1 | 12/2002 | van Lengerich |
| 6,514,547 B1 | 2/2003 | Hefnawy |
| 6,589,562 B1 * | 7/2003 | Shefer et al. ............... 424/490 |
| 2003/0017183 A1 * | 1/2003 | Pollock ..................... 424/401 |

* cited by examiner

MULTI COMPONENT CONTROLLED RELEASE SYSTEM FOR ORAL CARE, FOOD PRODUCTS, NUTRACEUTICAL, AND BEVERAGES This patent application is a continuation in part of U.S. application Ser. No. 09/696,148, filed Oct. 25, 2000, now U.S. Pat. No. 6,589,562 entitled "Multicomponent Biodegradable Bioadhesive Controlled Release System for Oral Care Products," the contents of which are incorporated by reference into this application.

BACKGROUND OF THE INVENTION

1. Field of the Invention

The present invention relates to multi component controlled release system that can be incorporated in oral care products, nutraceutical, food products and beverages to effectively encapsulate one or multiple active ingredients and sensory markers (i.e., flavors, cooling agents, sweeteners, etc.) and release multiple active ingredients in a consecutive manner, one after the other. The controlled release system of the present invention enhances the stability and bioavailability of wide range of flavors, sensory markers, and other active ingredients, prolongs their residence time in the oral cavity, controls their release characteristics, and prolongs the sensation of flavors and sensory markers in the mouth to provide long lasting organoleptic perception or long lasting mouthfeel. The invention further relates to oral care, food products, and beverages comprising the controlled release system of the present invention.

2. Description of the Related Art

Extensive effort has been directed in recent years towards controlling the release characteristics of various active ingredients flavors and sensory markers to prolong product shelf life and to prolong the sensation in the mouth during consumption of food products and beverages. Various methods and compositions have been described for providing enhanced stability and better control of the release of active ingredients and flavors in food products.

Spray drying, accounts for the majority of commercial encapsulated materials in food products. The spray drying encapsulation process is relatively simple, economical, and easily scaled to large production volumes. A major benefit of spray drying encapsulation is the broad range of actives and sensory markers which can be encapsulated. These actives include oil-soluble flavors, water-soluble compounds, natural extracts, single component flavor compounds, as well as complex compounded flavors having both water- and oil-soluble components.

U.S. Pat. No. 3,971,852 discloses the use of modified starch, gums and other natural hydro-colloids with lower molecular weight polyhydroxy compounds to yield a glassy cellular matrix with encapsulated oil at a maximum of 80 volume %. This system forms a shell surrounding the oil flavoring but is limited to lipophilic flavoring agents.

U.S. Pat. No. 4,532,145 describe a process and composition in which a volatile flavorant is fixed by spray drying from a carrier solution made up of 10–30% of a low molecular weight component such as a sugar or an edible food acid with the balance of solids being a maltodextrin carbohydrate in the amount of 70–90%.

U.S. Pat. No. 5,124,162 discloses a carrier mixture composed of mono- and disaccharides (22–45%), maltodextrins (25–50%), and a high molecular weight carbohydrate such as gum arabic, gum acacia or chemically modified starch (10–35%) to which flavoring agents are added and the subsequent solution spray dried to yield a free flowing powder with a bulk density of 0.50 g/cc.

U.S. Pat. No. 4,859,377 describes the use of amylose-containing pregelatinized starch to encapsulate entomopathogens, thereby protecting such biocontrol agents from environmental degradation and also promoting infection of target pests. The encapsulation is effected in an aqueous dispersion of the pregelatinized starch: for dry, granular products, the starch solids content of the dispersion is 25–40%; for sprayable liquid products, chemically degraded starch is used at a solids content of 1–10%.

U.S. Pat. No. 4,911,952 discloses chemical biological agents to be encapsulated are blended into an aqueous dispersion of an unmodified starch comprising about 5% to about 25% by weight amylose. The dispersion, having an initial starch solids content of about 20% by weight, is characterized by completely disrupted starch granules and completely disassociated amylose molecules that are not significantly depolymerized. Subsequent drying is accomplished by reassociation of the amylose molecules which converts the dispersion into a protective matrix and binds the agents within the interstices of the reassociating starch chains. Rate of release of agents to the environment can be altered by varying the proportion of amylose in the starch. Encapsulation of biologically active compositions provides protection against degradative environmental conditions, improves safety in handling, and slows the release of such compounds to the surrounding medium.

U.S. Pat. No. 5,183,690 discloses biologically active agents to be encapsulated are continuously blended with a starchy material and water, subjected to high-shear mechanical action at a temperature above the gelatinization temperature of starch, and continuously recovered as an insolubilized matrix of starch that entraps discontinuous domains of the agent. Alternatively, the core material to be encapsulated is added and blended with the aqueous dispersion of starch after the starch and water have been subjected to an elevated temperature sufficient to gelatinize the starch. Rate of release of agents to the environment can be controlled by preselecting a set of conditions related to various processing parameters. Encapsulation of biologically active compositions provides protection against degradative environmental conditions, improves safety in handling, and slows the release of such compounds to the surrounding medium.

U.S. Pat. No. 5,506,353 discloses particulate flavor composition comprising a flavor oil fixed in a particulate low cariogenic matrix of hydrogenated starch hydrolysate and a maltodextrin having a dextrose equivalent value of less than 20. A process for the encapsulation of a flavor oil comprising forming a homogeneous mixture of the flavor oil with (a) from about 40 to about 85 percent by weight of a particulate polyol consisting of hydrogenated starch hydrolysate, (b) from about 10 to about 30 percent by weight of a maltodextrin having a dextrose equivalent of less than 20, (c) an emulsifier and water, and spray-drying the resultant mixture to form a particulate product of from about 0.15 to about 0.85 g/cc bulk free flow density. Methods to confer, enhance or modify the flavor properties of a consumable edible material which comprises adding thereto the particulate flavor composition defined above; and methods to confer, enhance or modify the flavor properties of a tooth-paste base which comprises adding thereto the particulate flavor composition defined above are described.

An alternative process for encapsulation of active ingredients and sensory markers for food products is melt extrusion. In this process, a melting system, i.e. an extruder, is employed to form the carrier melt in a continuous process. The encapsulated flavor is either admixed or injected into the molten carbohydrate carrier.

U.S. Pat. No. 2,809,895 describes a process for encapsulation of an essential oil, such as lemon, lime or grapefruit oils, in a matrix comprising corn syrup, antioxidant and dispersing agent. The essential oil, antioxidant and dispersing agent are added to the corn syrup, the resultant mixture is heated to 85 degree–125 degree C. and agitated or extruded to form an emulsion in pellet form, and the resulting particles are washed with a solvent and finally dried.

Similarly, in U.S. Pat. No. 3,922,354, Galuzzi et al. disclose the use of high-shear mixing to incorporate active agents into low-water, high-solids matrices prepared from partially gelatinized unmodified starches. Additives such as modified dextrins, mixtures of mono- and diglycerides, toasted cereal solids, and coloring agents are used to control the release of active agents.

U.S. Pat. No. 4,232,047 teaches the preparation of a food supplement concentrate of an ingestible agent encased as a dispersed microphase in a matrix encapsulating medium, such as starch, protein, flour, modified starch, gum, or mixtures thereof. The concentrate is prepared by mixing the ingestible agent and the encapsulating medium with limited water to convert the mixture, under applied extrusion pressure and controlled heat. The protein exemplified is gelatin.

U.S. Pat. No. 4,230,687 discloses the application of shearing stress, vigorous mechanical working, and heat to distribute active agent into an enveloping matrix of chemically modified starches, gums, and proteins in the presence of a limited quantity of water. Proteins are used for slow-release matrices; modified starches are used for rapid release.

U.S. Pat. No. 4,420,534 describes the use of a matrix composition consisting of 10 to 30 wt % of a low molecular weight component chosen from a series of mono- or disaccharides, corn syrup solids, or organic acid with the balance of the mixture being maltodextrin. The matrix base is dry blended with an anhydrous liquid flavoring component and melted in a single screw extruder to yield a solid matrix characterized as a glass with a glass transition temperature >40° C.

U.S. Pat. No. 4,689,235 discloses an extrudable encapsulation matrix composition having improved loading capacity for oils, flavors, fragrances, agricultural chemicals, insecticides, drugs, etc. The matrix comprises a maltodextrin and hydrogen octenylbutanedioate amylodextrin or equivalent.

U.S. Pat. Nos. 4,610,890 and 4,707,367 disclose a solid essential oil flavor composition having a high essential oil content and a process for preparing the product are disclosed, the process involving preparation of a heated or cooked aqueous mixture of a sugar and starch hydrolyzate together with an emulsifier. A selected essential oil or other oil-soluble flavor is combined and blended with a mixture in a closed vessel under controlled pressure conditions to form a homogeneous melt, the melt being extruded into a relatively cool solvent, dried and combined with a selected anticaking agent to produce the stable, relatively non-hygroscopic particulate flavor composition of the invention. The selected quantity of essential oil flavor blended into the homogeneous melt being sufficient to yield about 12 to 35% by weight of essential oil in the encapsulated solid particulate composition. During the process, encapsulation efficiency is maintained preferably at or above about 60%, more preferably above about 70% and most preferably above about 75 to 80%. Also, the cook temperature for the process is preferably maintained at or below a maximum of about 126 degree C.

U.S. Pat. Nos. 4,610,890 and 4,707,367 describe a process for preparing a solid essential oil composition having a high content of the essential oil, which composition is prepared by forming an aqueous solution containing a sugar, a starch hydrolysate and an emulsifier. The essential oil is blended with the aqueous solution in a closed vessel under controlled pressure to form a homogeneous melt, which is then extruded into a relatively cold solvent, dried and combined with an anti-caking agent.

U.S. Pat. No. 4,929,447 discloses method and composition for protecting an active ingredient and providing controlled release therefore, especially in a chewing gum composition, which includes a high molecular weight polyvinyl acetate blended with a hydrophobic plasticizer which forms a film with the high molecular weight polyvinyl acetate in the absence of an added solvent therefore. The active ingredient, such as the artificial sweetener aspartame, is blended into the encapsulating composition as, for example, by melt blend which can then be cooled to a solid and ground into particulate. The encapsulated active ingredient can then be used in a composition for ingestion by a human in the form of, for example, a chewing gum with extended shelf life and highly controlled release of the active ingredient.

Encapsulation of components in a grindable, glassy carbohydrate matrix is disclosed in U.S. Pat. Nos. 5,009,900 and 5,087,461 and U.S. Pat. Nos. 5,972,404 and 6,004,594. In U.S. Pat. Nos. 5,009,900 and 5,087,461 volatile and/or labile components, such as vitamins or flavoring components, are encapsulated in extruded glassy matrices comprising a water-soluble, chemically-modified starch having a dextrose equivalent not greater than about 2, a maltodextrin having a dextrose equivalent in the range of from about 5 to about 15, corn syrup solids or a polydextrose having a dextrose equivalent in the range of from about 21 to about 42, and a mono- or disaccharide.

U.S. Pat. Nos. 6,468,568 and 6,436,453 disclose a mineral or vitamin fortification ingredient which does not deleteriously affect palatability and appearance of foods is obtained by encapsulation of the mineral or vitamin in a grindable, glassy matrix composition. The glassy matrix composition includes an oligosaccharide, such as beta-2-1 fructofuranose materials, preferably fructooligosaccharides (FOS) and inulin, which not only forms a glassy matrix, but also beneficially increases the fiber content of the food. At least one edible oil is included in the encapsulating composition to prevent substantial adverse interaction between the mineral or vitamin encapsulant and the glass-forming oligosaccharide matrix material, and to achieve controlled release of the encapsulant from the glassy matrix. A method for encapsulating a mineral or vitamin in a glassy matrix is described comprising: a. admixing an encapsulant component comprising at least one mineral or vitamin with an edible oil to obtain a slurry wherein said at least one mineral or vitamin is encapsulated by said oil, b. admixing said slurry with a melt comprising at least one molten glass-forming oligosaccharide matrix component to obtain a molten blend, and c. cooling the molten blend to encapsulate the oil encapsulated mineral or vitamin in a glassy matrix.

U.S. Pat. Nos. 5,897,897, 6,187,351, and 6,416,799 disclose carbohydrate-based glassy matrices which are stable in the glassy state at ambient temperatures may be prepared by the use of aqueous plasticizers with melt extrusion. Such glassy matrices are useful for the encapsulation of encapsulates, in particular, flavoring agents.

Coacervation is another encapsulation technology that was commercialized in the 1950s, yields that has found wide usage in the pharmaceutical, fragrance and specialty products industries. However the relatively high process costs, sensitive multi-step batch process, regulations limiting the number of polymeric agents which can be used in food preparations, and the difficulty in dealing with encapsulates having both aqueous and lipid solubility properties has drastically limited the application of coacervation for flavor encapsulation in the food industry. A general discussion of these issues is provided by R. Versic, "Coacervation for Flavor Encapsulation," in Flavor Encapsulation, American Chemical Society Symposium Series #370, S. Risch and G. Reneccius, Eds., Chapter 14, 1988, which is incorporated herein by reference. Coacervation microcapsule systems can be generated in the form of simple coacervates, which are derived from a single polymer species in solution. Complex coacervates, which require the interaction of two distinct and oppositely charged polymer species, are also well characterized.

U.S. Pat. No. 3,962,463 discloses the encapsulation of flavor ingredients in gelatin waxes, polyethylene and the like followed by the depositing of the encapsulated flavor particles on the surface of the chewing gum. U.S. Pat. No. 4,217,368 discloses the controlled release of a (second) sweetener which is dispersed in, enveloped by, trapped in and otherwise protected by the gum base. A first sweetener, which is relatively unprotected, provides an initial burst of flavor. U.S. Pat. No. 4,259,355 discloses a hydrolytically releasable flavor oil entrapped in gelatine, dextrin, gum acacia or modified food starch with the aid of a hydroxypropylcellulose solid suspending agent.

U.S. Pat. No. 4,230,687 discloses the encapsulation of flavoring agent in a polymeric medium using rigorous and intimate conditions of mechanical shear to mix the flavoring agent with the encapsulating medium. The flavoring agent is gradually released from the encapsulating matrix at a rate dependent upon the rate of hydration of the matrix, which in turn depends upon the particular matrix used. The polymeric matrix may be derived from natural substances such as casein, a gelatin, modified starches, gums and related materials.

Complex coacervation encapsulation, which yields oil droplets surrounded by a chemically crosslinked polymer film has been utilized for the encapsulation of cinnamon oil in chewing gums as disclosed in U.S. Pat. No. 5,266,335.

U.S. Pat. No. 5,418,010 discloses a microencapsulation process in which a solid or liquid core material is dispersed in a protein slurry, is heated to create a protein melt and then denatured to bring about encapsulation of the core material and the product of that process.

U.S. Pat. No. 6,428,827 discloses methods and compositions for improving the flavor duration in chewing gum. In a preferred form, the present invention provides matrix compositions comprising a hydroxypropylcellulose crosslinked with a multi-functional carboxylate to yield a matrix having lower water solubility than the original cellulosic material. This matrix may be ground up, have a flavor incorporated therein and used in gum compositions in which it facilitates a prolonged release of the flavoring.

Coating or fat coating is another encapsulation technique that has been employed. Conventionally, such fat coatings are applied via a fluidized bed technique. This technique suffers from serious shortcomings, such as exposure of the active agent to a vigorous air stream that will result in that significant active agents may either volatilize or oxidize under such conditions. This air contacting may occur over a long time period as the rate of fat addition must often be slow, as it is determined by the heat load the air stream can carry away. This also limits the overall productivity of fluid-bed techniques, which in turn influences processing costs and ultimately commercial utility. In addition, the protection afforded by fat coatings applied as described above, or using any method, may be easily lost when the fat-coated particle is exposed to temperatures above the melting point of the fat.

U.S. Pat. No. 3,976,794 shows sweetened coconut products coated with a powdered sugar containing particles of sugar coated in edible fat. U.S. Pat. Nos. 3,949,094 and 3,949,096 show a process for preparing various flavorings, colorants, and flavor enhancers coated with various fats and emulsifiers, the process comprising spraying condiments which are intercepted by a second spray of certain edible coating materials.

In U.S. Pat. No. 4,765,996 polished rice or barley is enriched with nutrients which are fixed in and on the grain by coating an oil/fat and/or a wax on the grains, coating the same with a hydrophilic emulsifier and further coating them with a starch-based coating agent.

U.S. Pat. No. 5,500,223 discloses an encapsulation process employs an aqueous dispersion of silica having a particle size not substantially greater than 100 nm. An emulsion is formed by high shear mixing of the silica dispersion with the material to be encapsulated and the emulsion is gelled. The process allows hydrophobic materials to be encapsulated in structures which have a high loading of the material and a good degree of imperviousness in the presence of other materials such as surfactants and mineral oils. Using the process, hydrophobic materials such as flavors, fragrances and cosmetic ingredients can be encapsulated for delayed release in a wide variety of products.

U.S. Pat. No. 6,165,516 discloses a method for producing a chewing gum with a controlled release of caffeine, as well as the chewing gum so produced, is obtained by physically modifying caffeine's properties by coating and drying. Caffeine is coated by encapsulation, partially coated by agglomeration, entrapped by absorption, or treated by multiple steps of encapsulation, agglomeration, and absorption. The coated caffeine is then co-dried and particle sized to produce a release-modified caffeine. When incorporated into the chewing gum, these particles are adapted to produce a fast release or a delayed release when the gum is chewed.

U.S. Pat. No. 4,971,797 discloses stabilized sucralose complex in a thermally stable composition by co-crystallization with a cyclodextrin. The resulting crystalline product may be comminuted to form particles of desired size for use as a sweetener component in place of or in addition to known sweeteners such as sucrose, saccharin and the like, in a variety of foods, comestibles, and oral medications. The preparation of the stabilized sucralose compositions of the present invention constitutes a molecular encapsulation of the sucralose within the cyclodextrin thereby protecting the sucralose from discoloration caused by heat.

Spray-chilling is another form of encapsulation practiced commercially. This process begins with mixing a liquid flavor into a molten fat to create a solution/dispersion. The resulting mixture is then atomized into a chamber where it is contacted with an air stream which is cool enough to cause the atomized droplets to solidify, thus forming a crude encapsulated product. The major drawbacks of spray-chilling include fat/active-agent interactions, volatilization over time of lipid soluble materials, as well as loss of volatile materials during processing.

U.S. Pat. No. 5,064,669 discloses controlled release flowable flavoring powders and processes and apparatus for preparing and using such agents, the processes comprising heating a high melting point encapsulating or enrobing material, such as a fat and/or wax and one or more emulsifiers to melt this starting material; mixing one or more water-containing flavor compositions with a texture conditioning agent; mixing the flavor compositions and texture conditioning agent(s) with the molten fat or wax to obtain a homogeneous mixture in the form of an emulsion; and chilling the flavor composition-containing mixture to provide discrete particles of solid encapsulated flavoring agent, together with the products so produced and methods for using same.

U.S. Pat. No. 6,245,366 discloses a fat-coated encapsulation compositions may be prepared by: (i) mixing an active agent with a molten fat, to obtain a slurry, and (ii) cooling the slurry, to obtain a solid mass in which the active agent is dispersed in solid fat.

U.S. Pat. No. 6,328,988 discloses polymeric micelles for encapsulation of hydrophobic molecules are provided. Methods and formulations for delivering hydrophobic molecules to a host via these micelles are also provided. Methods of stabilizing liposomes or lipid based formulations by addition of polymeric micelles are also provided.

Accordingly, there remains a need in the art to provide methods and compositions using an efficient and economical process that can be incorporated in food products and beverages to effectively encapsulate one or multiple active ingredients and sensory markers (i.e., flavors, cooling agents, etc.), enhance their stability and bioavailability, control their release characteristics, prolong their sensation in the mouth during consumption of food products and beverages to provide a long lasting organoleptic perception or long lasting mouthfeel, and release multiple active ingredients in a consecutive manner.

SUMMARY OF THE INVENTION

The present invention relates to an improved controlled release system that can be incorporated in oral care, food products, and beverages that can effectively encapsulate one or more types of active ingredients, flavors, or combinations of flavors and various active ingredients to release them one after the other in a consecutive manner or to provide change in flavor character. The controlled release system of the present invention can encapsulate a broad range of active ingredients and sensory markers (i.e., flavors, cooling agents, sweeteners, etc.), to enhance their stability and bioavailability, prolong their residence time in the oral cavity, control their release characteristics, and prolong their sensation in the mouth during consumption of food products and beverages to provide a long lasting organoleptic perception or long lasting mouthfeel.

The controlled release system of the present invention comprises solid hydrophobic nanospheres encapsulated in a moisture sensitive microsphere. The nanospheres are not individually coated by the moisture sensitive microspheres matrix, but are homogenously dispersed in the water sensitive microsphere matrix. Various flavors and active ingredients can be incorporated in the hydrophobic nanosphere matrix, in the water sensitive microsphere matrix, or in both the nano and micro spheres matrices. The active ingredients, flavors, and sensory markers encapsulated in the nanospheres can be the same or different than those encapsulated in the microspheres. The nanosphere surface can include a bioadhesive to improve the deposition and prolong the residence time of the nanospheres in the oral cavity. Alternatively, a bioadhesive polymer can be incorporated in the water sensitive microsphere matrix to create the bioadhesive properties of the nanospheres.

The microspheres have an average sphere size in the range from about 20 microns to about 100 microns. The nanosphere have an average sphere size in the range from about 0.01 micron to about 5 microns and having a melting point in the range from about 30° C. to about 90° C. A first flavor, or active ingredient can be encapsulated in a water sensitive microsphere and released upon exposure of the system to moisture (wetting the lips, in the mouth, and the like) and a second flavor, or active ingredient can be encapsulated in the solid hydrophobic nanospheres and released over an extended period of time. In addition, the production of the controlled release system utilizes minimum processing steps and is efficient and economical.

The controlled release system of the present invention is a free-flowing powder formed of solid hydrophobic nanospheres comprising flavors, sensory markers, and other various active ingredients, that are encapsulated in a moisture sensitive microsphere that can also contain flavors, sensory markers, and other various active ingredients. The active ingredients encapsulated in the nanospheres can be the same or different from those encapsulated in the microsphere. The controlled release system of the present invention is characterized by:

(i) protection of the active ingredients, as well as the volatile constituents of flavors, during storage, until needed;

(ii) enhanced bioavailability of various active ingredients, such as vitamins, biologically active agents, nutrients, and others;

(iii) moisture triggered release of the flavors, and other active ingredients that are encapsulated in the microsphere water sensitive matrix, as well as, the nanospheres comprising the same or other flavors, and active ingredients;

(iv) change in flavor character or other olfactory sensation in response to moisture;

(v) prolonged release of flavors, and other active ingredients that are encapsulated in the solid hydrophobic nanospheres, over an extended period of time; and (vi) long lasting organoleptic perception or long lasting mouthfeel of flavors, sensory markers, sweeteners, and other active ingredients.

The controlled release system of the present invention improves the stability of various active ingredients and flavors or flavor ingredients in food products and beverages, protects them against the development of off-flavors and off odors such as protect citral and citrus notes against oxidation, preventing the development of off-flavors and off odors, and increasing the shelf life of food and beverage products.

The present invention also provides a method for producing the multi component controlled release system of the present invention comprising the steps of:

(i) incorporating the flavor, and other active ingredients into the solid hydrophobic nanospheres;

(ii) forming an aqueous mixture comprising of one or more flavor, and other active ingredients, the nanospheres, and a water sensitive material, such as, starch derivatives, natural gums, polyvinyl alcohol, proteins, hydrocolloids, or mixture of thereof; and (iii) spray drying the mixture to form a dry powder composition.

The invention further provides a process for producing the multi component controlled release system for food products and beverage including the flavors, and other active ingredients comprising the steps of:

(i) heating one or more hydrophobic materials to a temperature above the melting point of the materials to form a melt;

(ii) dissolving or dispersing a first flavor into the melt;

(iii) dissolving or dispersing a first one or more active ingredients into the melt;

(iv) dissolving or dispersing a second flavor, active ingredients, and moisture sensitive materials, such as, starch derivatives, natural gums, polyvinyl alcohol, proteins, hydrocolloids, or mixture of thereof, in the aqueous phase;

(v) heating the composition to above the melting temperature of the hydrophobic materials; mixing the hot melt with the aqueous phase to form a dispersion;

(vi) high shear homogenization of the dispersion at a temperature above the melting temperature until a homogeneous fine dispersion is obtained;

(vii) cooling the dispersion to ambient temperature; and
(viii) spray drying the emulsified mixed suspension to form a dry powder composition.

Oral care, food products or beverages incorporating the multi component system of the present invention that comprises different flavors or sensory markers in the nanospheres and the microspheres was found to provide a perceivable flavor transition (change in flavor character) or change in the organoleptic perception in response to moisture or change in the organoleptic perception, in response to moisture as well as prolonged flavor perception and mouthfeel. The multi component system of the present invention was found to extend the release rate of the flavors, sensory markers, and the active ingredients that were encapsulated in the solid hydrophobic nanospheres over an extended period of time to provide long lasting organoleptic perception or long lasting mouthfeel of flavors, sensory markers, sweeteners, and other active ingredients. In an alternate embodiment, a controlled release composition for food products and beverages is formed of hydrophobic nanospheres incorporating flavors, sensory markers, and other active agents.

The multi-component controlled release system of the present invention can comprise from about 1% to about 50% by weight of a hydrophobic matrix, from about 1% to about 50% by weight of a water sensitive matrix, and from about 1% to about 50% by weight flavor, or other active ingredients.

The present invention addresses the foregoing need for food products and beverages that provide special performance features to enhance product performance and differentiate the product from that of the competitors and provide long-term storage stability. The invention will be more fully described by reference to the following drawing.

DETAILED DESCRIPTION

The present invention provides a method to enhance the performance of food products, beverages, and other oral care compositions. The invention relates to a controlled release system that can provide a perceivable flavor transition (change in flavor character) or change in the organoleptic perception in response to moisture during the use of the product and extend flavor perception and mouthfeel over an extended period of time.

Figure 1:
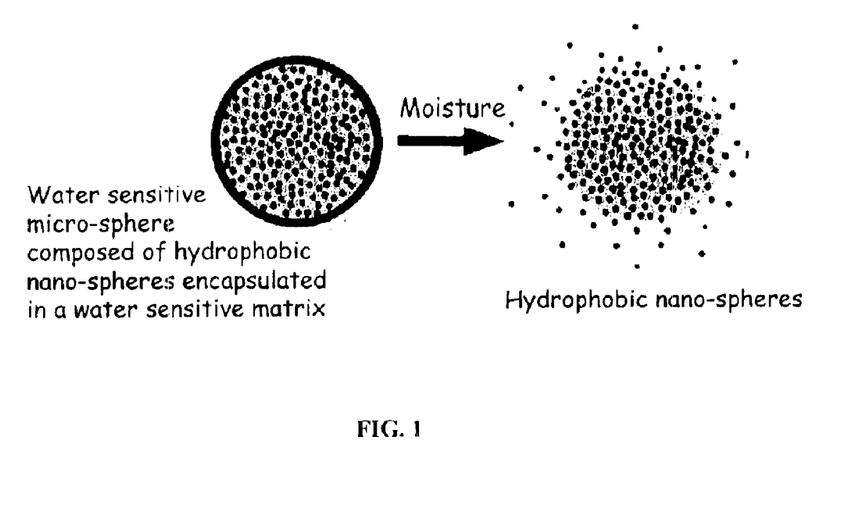
FIG. 1 is a schematic diagram of a controlled release system of the present invention.

The controlled release system of the present invention is a free-flowing powder formed of solid hydrophobic nanospheres comprising one or more of flavors, sensory markers, and active ingredients that are encapsulated in a moisture sensitive microsphere that can also encapsulate the same or other flavors, sensory markers, and active ingredients, as shown in FIG. 1. The term "spheres" is intended to describe solid, substantially spherical particulates. It will be appreciated that other shapes can be formed in accordance with the teachings of the present invention.

The nanospheres of the present invention have an average diameter in the range from about 0.01 micron to about 10 microns. Preferably, the sphere size of the nanospheres is in the range from about 0.05 microns to about 2 microns. This linear dimension for any individual sphere represents the length of the longest straight line joining two points on the surface of the sphere.

Additional vitamins, biologically or nutritionally active components, edible active ingredients, and pharmaceutical active ingredients can be added to the controlled release system of the present invention.

Nutraceutical components can include components which promote health or prevent disease or enhance well-being such as antioxidants, phytochemicals, hormones, vitamins such as Vitamins A, B1, B2, B6, B12; C, D, E, K, pantothenate, folic acid, pro-vitamins, minerals such as calcium, selenium, magnesium salts, available iron, and iron salts, microorganisms such as bacteria, such as live lactobacilli, fungi, and yeast, prebiotics, probiotics, trace elements, essential and/or highly unsaturated fatty acids such as omega-3 fatty acids, and mid-chain triglycerides, nutritional supplements, enzymes such as amylases, proteases, lipases, pectinases, cellulases, hemicellulases, pentosanases, xylanases, and phytases, pigments, oligopeptides, dipeptides, and amino acids, and mixtures thereof The multi-component release system of the present invention can be used in food products. The term "food product" refers to material of either plant or animal origin or of synthetic sources that contain a body nutrient such as a carbohydrate, protein, fat vitamin, mineral, etc. The multi-controlled release system of the present invention can be incorporated into foods intended for human or animal consumption such as baked goods, for example, bread, wafers, cookies, crackers, pretzels, pizza, and rolls, ready-to-eat breakfast cereals, hot cereals, pasta products, snacks such as fruit snacks, salty snacks, grain-based snacks, and microwave popcorn, dairy products such as yogurt, cheese, and ice cream, sweet goods such as hard candy, soft candy, and chocolate, animal feed, pet foods such as dog food and cat food, aqua-culture foods such as fish food and shrimp feed, and special purpose foods such as baby food, infant formulas, hospital food, medical food, sports food, performance food or nutritional bars, or fortified foods, food pre-blends or mixes for home or food service use, such as pre-blends for soups or gravy, dessert mixes, dinner mixes, baking mixes such as bread mixes, and cake mixes, and baking flour. The discrete particulates of the present invention may be used as a topping for breakfast cereals, snacks, soups, salad, cakes, cookies, crackers, puddings, desserts or ice cream. They may also be used as a granular ingredient for yogurts, desserts, puddings, custards, ice cream or other pasty or creamy foods. The food products can include for example, baking products such as chocolate, sauces and soups or the like.

If a final product is a baked good the release system of the present invention will be mixed with other conventional baking ingredients and then baked to provide the final product. The multi-component controlled release system of the present invention can be used in beverages such as powdered drink mixes and liquid drinks.

For example, the multi-component controlled release system of the present invention can be employed in hydratable sauces and soups. Sauces and soups according to the invention, can be made in a brand variety of flavors and textures. Various flavors can be encapsulated in the multi-component controlled release system of the present invention depending upon the desired flavor and texture of the sauce or soup when the sauce or soup is hydrated. Flavor ingredients can include crystalline ingredients such as sugar, salt, citric acid and substitutes therefor; dairy ingredients such as dry milk, cheeses, cream powders and the like;

spices, natural and artificial flavors, and thickening agents such as starches (native, modified, waxy, etc.), protein compounds (e.g., albumin, globulin, egg protein or whey protein concentrate) and vegetable gums and any combination thereof.

The multi-component controlled release system can be used in beverages. For example, powder drink mixes can employ the controlled release system of the present invention.

If a powdered drink mix is desired, the controlled release system of the present invention can encapsulate flavorants and be blended with suspending agents and the like to form a final dry mix product. To produce a liquid drink the controlled release system of the present invention can encapsulate flavorants and can be mixed with liquid, e.g. water and other ingredients such as suspending agents and the like to produce the final drink product.

The multi-component controlled release system of the present invention can be used in a nutraceutical. The term "nutraceutical" refers to any compounds or chemicals that can provide dietary or health benefits when consumed by humans or animals. Examples of nutraceuticals include vitamins, minerals and others.

The biodegradable multi-component controlled release system provided by the present invention can generally be incorporated into any suitable conventional oral hygiene product. Exemplary delivery systems include gels, chewing gums, toothpaste, and mouthwash. The toothpaste can include other conventional components such as an abrasive such as, silica or alumina, having a particle size of between about 5 microns and about 50 microns, a thickener such as, colloidal silica having a particle size of between about 0.1 microns and about 1 micron, and neat flavor oil. The oral hygiene product can be appropriately selected depending upon the physical location for delivery of the nano-particles and the intended use of the nano-particles. The above-described exemplary delivery systems are preferred in accordance with the present invention, since they permit effective delivery of the bioadhesive nano-particles into the oral cavity.

The additional components are usually present in an amount from about 1% to about 20% by weight of the spheres.

I. Matrix Materials for Forming the Nanospheres

Considerations in the selection of the matrix material include good barrier properties to the active ingredients, low toxicity and irritancy, stability, integrity, and high loading capacity for the active agents of interest. Suitable wax materials for the compositions and devices of the present invention are inert nontoxic materials with a melting point range between about 30° C. and about 90° C. and penetration point of about 1 to about 10. Examples of wax materials include natural waxes, synthetic waxes and mixtures thereof. Suitable waxes also include natural, regenerated, or synthetic food approved waxes including animal waxes such as beeswax, vegetable waxes such as carnauba, candelilla, sugar cane, rice bran, and bayberry wax, mineral waxes such as petroleum waxes including paraffin and microcrystalline wax, and mixtures thereof.

Other wax materials that are known to those skilled in the art and suitable materials as described in "Industrial Waxes" Vol. I and II, by Bennett F. A. I. C., published by Chemical Publishing Company Inc., 1975 and Martindale, "The Extra Pharmacopoeia", The Pharmaceutical Press, $28^{th}$ Edition pp. 1063–1072, 1982 can be used in the present invention.

Suitable fat materials and/or glyceride materials which can be used in the present invention include, but are not limited to, the following classes of lipids: mono-, di and triglycerides, phospholipids, sphingolipids, cholesterol and steroid derivatives, terpenes and vitamins. Examples of solid fat materials which can be used in the present invention, include solid hydrogenated castor and vegetable oils, hard fats, and mixtures thereof. Other fat materials which can be used, include triglycerides of food grade purity, which can be produced by synthesis or by isolation from natural sources. Natural sources can include animal fat or vegetable oil, such as soy oil, as a source of long chain triglycerides (LCT). Other triglycerides suitable for use in the present invention are composed of a majority of medium length fatty acids (C10–C18), denoted medium chain triglycerides (MCT). The fatty acid moieties of such triglycerides can be unsaturated or polyunsaturated and mixtures of triglycerides having various fatty acid material. Steroids which can be used include as fat materials, but are not limited to, cholesterol, cholesterol sulfate, cholesterol hemisuccinate, 6-(5-cholesterol 3 beta-yloxy) hexyl6-amino-6-deoxy-1-thio-alpha-D-galactopyranoside, 6-(5-cholesten-3 beta-tloxy)hexyl-6-amino-6-deoxyl-1-thio-alpha-D mannopyranoside and cholesteryl)4'-trimethyl 35 ammonio)butanoate.

The fat material can be fatty acids and derivatives thereof which can include, but are not limited to, saturated and unsaturated fatty acids, odd and even number fatty acids, cis and trans isomers, and fatty acid derivatives including alcohols, esters, anhydrides, hydroxy fatty acids and prostaglandins. Saturated and unsaturated fatty acids that can be used include, but are not limited to, molecules that have between 12 carbon atoms and 22 carbon atoms in either linear or branched form. Examples of saturated fatty acids that can be used include, but are not limited to, lauric, myristic, palmitic, and stearic acids. Examples of unsaturated fatty acids that can be used include, but are not limited to, lauric, physeteric, myristoleic, palmitoleic, petroselinic, and oleic acids. Examples of branched fatty acids that can be used include, but are not limited to, isolauric, isomyristic, isopalmitic, and isostearic acids and isoprenoids. Fatty acid derivatives include 12-(((7'-diethylaminocoumarin-3yl) carbonyl)methylamino)-octadecanoic acid; N-[12-(((7'diethylaminocoumarin-3-yl)carbonyl)methyl-amino) octadecanoyl]-2-aminopalmitic acid, N succinyl-dioleoylphosphatidylethanol amine and palmitoyl-homocysteine; and/or combinations thereof. Mono, di and triglycerides or derivatives thereof that can be used include, but are not limited to, molecules that have fatty acids or mixtures of fatty acids between 6 and 24 carbon atoms, digalactosyldiglyceride, 1,2-dioleoyl-sn-glycerol; 1,2-cdipalmitoyl-sn-3 succinylglycerol; and 1,3-dipalmitoyl-2-succinylglycerol.

Surfactants can also be incorporated into the hydrophobic matrix generally include all food approved and pharmaceutically-acceptable surfactants Sodium lauryl sulfate is a water-soluble salt, produced as a white or cream powder, crystals, or flakes. Also known as dodecyl sodium sulfate, sodium lauryl sulfate can be a mixture of sodium alkyl sulfates consisting chiefly of sodium lauryl sulfate. Sodium lauryl sulfate is also known as sulfuric acid monododecyl ester sodium salt. Furthermore, sodium lauryl sulfate is readily available from commercial sources such as Sigma or Aldrich in both solid form and as a solution. The solubility of sodium lauryl sulfate is about 1 gm per 10 ml/water. The fatty acids of coconut oil, consisting chiefly of lauric acid, are catalytically hydrogenated to form the corresponding alcohols. The alcohols are then esterified with sulfuric acid (sulfated) and the resulting mixture of alkyl bisulfates (alkyl sulfuric acids) is converted into sodium salts by reacting with alkali under controlled conditions of pH.

Alternative anionic surfactants for use as surface active agents in the present invention include docusate salts such as the sodium salt thereof. Other suitable anionic surfactants include, without limitation, alkyl carboxylates, acyl lactylates, alkyl ether carboxylates, N-acyl sarcosinates, polyvalent alkyl carbonates, N-acyl glutamates, fatty acid, polypeptide condensates and sulfuric acid esters.

In other aspects of the invention amphoteric (amphipathic/amphiphilic surfactants), non-ionic surfactants and/or cationic surfactants can be used as the surface active agent in the coprocessed compositions of the present invention. Suitable pharmaceutically-acceptable non-ionic surfactants include, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone.

Other suitable pharmaceutically-acceptable surfactants include acacia, benzalkonium chloride, cholesterol, emulsifying wax, glycerol monostearate, lanolin alcohols, lecithin, poloxamer, polyoxyethylene, and castor oil derivatives.

The nanospheres of the present invention can have a melting point in the range from about 30° C. to about 90° C., preferably from about 40° C. to about 90° C. The melting point of the spheres is usually a function of the carrier matrix employed. Accordingly, preferred matrix materials have a melting point in the range of about 50° C. to about 80° C., preferably from about 60° C. to about 70° C. It should be understood that it is the melting point of the sphere rather than of the carrier matrix that is important for use of the carrier system of the present invention.

II. Matrix Materials for Forming the Microspheres
Moisture-Sensitive and Bioadhesive Materials Moisture-sensitive materials for forming the microspheres of the present invention comprise water soluble and water dispersible synthetic polymers and copolymers, starch derivatives, polysaccharides, hydrocolloids, natural gums, proteins, and mixtures thereof.

Examples of synthetic water sensitive polymers which are useful for the invention include polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester.

Examples of water soluble hydroxyalkyl and carboxyalkyl celluloses include hydroxyethyl and carboxymethyl cellulose, hydroxyethyl and carboxyethyl cellulose, hydroxymethyl and carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose, and the like. Also useful are alkali metal salts of these carboxyalkyl celluloses, particularly and preferably the sodium and potassium derivatives.

Polyvinyl alcohol useful in the practice of the invention is partially and fully hydrolyzed polyvinyl acetate, termed "polyvinyl alcohol" with polyvinyl acetate as hydrolyzed to an extent, also termed degree of hydrolysis, of from about 75% up to about 99%. Such materials are prepared by means of any of Examples I–XIV of U.S. Pat. No. 5,051,222 issued on Sep. 24, 1991, the specification for which is incorporated by reference herein.

A polyvinyl alcohol useful for practice of the present invention is Mowiol® 3-83, having a molecular weight of about 14,000 Da and degree of hydrolysis of about 83%, Mowiol® 3-98 and a fully hydrolyzed (98%) polyvinyl alcohol having a molecular weight of 16,000 Da commercially available from Gehring-Montgomery, Inc. of Warminister Pa. Other suitable polyvinyl alcohols are: AIRVOL® 205, having a molecular weight of about 15,000–27,000 Da and degree of hydrolysis of about 88%, and VINEX® 1025, having molecular weight of 15,000–27,000 Da degree of hydrolysis of about 99% and commercially available from Air Products & Chemicals, Inc. of Allentown, Pa.;

ELVANOL® 51-05, having a molecular weight of about 22,000–26,000 Da and degree of hydrolysis of about 89% and commercially available from the Du Pont Company, Polymer Products Department, Wilmington, Del.; ALCOTEX® 78 having a degree of hydrolysis of about 76% to about 79%, ALCOTEX® F88/4 having a degree of hydrolysis of about 86% to about 88% and commercially available from the Harlow Chemical Co. Ltd. of Templefields, Harlow, Essex, England CM20 2BH; and GOHSENOL® GL-03 and GOHSENOL® KA-20 commercially available from Nippon Gohsei K.K., The Nippon Synthetic Chemical Industry Co., Ltd., of No. 9-6, Nozaki Cho, Kita-Ku, Osaka, 530 Japan.

Suitable polysaccharides are polysaccharides of the non-sweet, coloidally-soluble types, such as natural gums, for example, gum arabic, starch derivates, dextrinized and hydrolyzed starches, and the like. A suitable polysaccharide is a water dispersible, modified starch commercially available as Capule®, N-Lok®, Hi-Cap™ 100 or Hi-Cap™ 200 commercially available from the National Starch and Chemical Company of Bridgewater, N.J.; Pure-Cote™, commercially available from the Grain Processing Corporation of Muscatine, Iowa. In the preferred embodiment the natural gum is a gum arabic, commercially available from TIC Gums Inc. Belcamp, Midland. Suitable hydrocolloids are xanthan, maltodextrin, galactomanan or tragacanth, preferably maltodextrins such as Maltrin™ M100, and Maltrin™ M150, commercially available from the Grain Processing Corporation of Muscatine, Iowa.

Enhancing the deposition of the nanospheres onto either the epithelial surface or the mucus can increase their residence time in the oral cavity and increase pharmaceutical and medical aspects of bioadhesive systems for drug delivery. Incorporating bioadhesive polymers in the nanosphere or the microsphere matrix can be utilized to control or increase the absorption of the nanosphere through the mucosal lining, or to further delay transit of the nanosphere through the gastrointestinal passages.

A bioadhesive polymer as used in the disclosure is one that binds to mucosal epithelium under normal physiological conditions. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues can be achieved by (i) physical or mechanical bonds, (ii) primary or covalent chemical bonds, and/or (iii) secondary chemical bonds such as ionic. Physical or mechanical bonds can result from deposition and inclusion of the bioadhesive material in the crevices of the mucus or the folds of the mucosa. Secondary chemical bonds, contributing to bioadhesive properties, can comprise dispersive interactions such as Van der Waals interactions and stronger specific interactions, such as hydrogen bonds. Hydrophilic functional groups primarily responsible for forming hydrogen bonds include hydroxyl and the carboxylic groups. Suitable bioadhesive polymers for use in the present invention include bioerodible hydrogels as described by H. S. Sawhney, C. P. Pathak and J. A. Hubell in Macromolecules. 1993, 26:581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly (butyl methacrylate), poly(isobutyl methacrylate), poly(hexl methacrylate), poly(isodecl methacrylate), poly(lauryl methacrylate), poly(phenyl methacrylate), poly(methyl acrylate), poly(isopropyl acrylate), poly(isobutyl acrylate), and poly(octadecl acrylate) and poly(fumaric-co-sebacic)acid.

Polymers with enhanced bioadhesive properties can be provided wherein anhydride monomers or oligomers are incorporated into the polymer. The oligomer excipients can be blended or incorporated into a wide range of hydrophilic and hydrophobic polymers including proteins, polysaccharides and synthetic biocompatible polymers. Anhydride oligomers can be combined with metal oxide particles to improve bioadhesion in addition to the use of organic additives alone. Organic dyes because of their electronic charge and hydrophobicity/hydrophilicity can either increase or decrease the bioadhesive properties of polymers when incorporated into the polymers. The incorporation of oligomer compounds into a wide range of different polymers which are not normally bioadhesive can be used to increase the adherence of the polymer to tissue surfaces such as mucosal membranes.

III. Flavors, Sensory Markers, and Other Active Ingredients

Various flavors and active ingredients can be incorporated in the hydrophobic nanosphere matrix, in the water sensitive microsphere matrix, or in both the nano and micro spheres matrices. The active ingredients, flavors, and sensory markers encapsulated in the nanospheres can be the same or different than those encapsulated in the microspheres. Flavors can be included in the controlled system of the present invention. The flavors that can be encapsulated in the system of the present invention can be any flavor material and can be selected according to the desires of the flavor creator. In general terms, such flavor materials are characterized by a vapor pressure below atmospheric pressure at ambient temperatures. The high boiling flavor materials employed herein will most often be solids at ambient temperatures, but also can include high boiling liquids. A wide variety of chemicals are known for flavor uses, including materials such as aldehydes, ketones, esters, and the like. More commonly, naturally occurring plant and animal oils and exudates comprising complex mixtures of various chemical components are known for use as flavors and such materials can be used herein. Flavors useful for the present invention can be a single aroma chemical, relatively simple in their composition, or can comprise highly sophisticated, complex mixtures of natural and synthetic chemical components, all chosen to provide any desired flavor.

Flavor materials suitable for use in the present invention are described more fully in S. Arctander, Perfume Flavors and Chemicals, Vols. I and II, Aurthor, Montclair, N.J. and the Merck Index, 8th Edition, Merck & Co., Inc. Rahway, N.J., both references being incorporated herein by reference.

Suitable cooling agents which can be included in the controlled release system of the present invention include menthol, non-volatile menthol analogs such as menthyl lactate, menthyl ethoxyacetate, menthone glycerinacetal, 3-1-menthoxypropane-1,2-diol, ethyl 1-menthyl carbonate, (1S,3S,4R)-p-menth-8-en-3-ol, menthyl pyrrolidone carboxylate, N-substituted-p-menthane-3-carboxamides (as described in U.S. Pat. No. 4,136,163, which is incorporated herein by reference) including, for example, N-ethyl-p-menthane-3-carboxamide, (such acyclic carboxamides being described in U.S. Pat. No. 4,153,679, which is incorporated herein by reference) including, for example, N,2,3-trimethyl-2-isopropylbutanamide, and ketal coolants (as described in WO 93/23005, which is incorporated herein by reference) including, for example, 1-menthon-1d-isomenthon glycerin ketal. Suitable cooling agents which can be used are 3-1-menthoxypropane-1,2-diol, N-ethyl-p-menthane-3-carboxamide (WS-3), N,2,3-trimethyl-2-isopropylbutanamide (WS-23), menthyl lactate (Frescolat ML), menthone glycerinacetal (Frescolat MGA) and menthyl ethoxyacetate (Menglytate).

Additional vitamins, biologically or nutritionally active components, edible active ingredients, and pharmaceutical active ingredients can be added to the controlled release system of the present invention.

Nutraceutical components may include components which promote health or prevent disease or enhance well-being such as antioxidants, phytochemicals, hormones, vitamins such as Vitamins A, B1, B2, B6, B12; C, D, E, K, pantothenate, folic acid, pro-vitamins, minerals such as calcium, selenium, magnesium salts, available iron, and iron salts, microorganisms such as bacteria, such as live lactobacilli, fungi, and yeast, prebiotics, probiotics, trace elements, essential and/or highly unsaturated fatty acids such as omega-3 fatty acids, and mid-chain triglycerides, nutritional supplements, enzymes such as amylases, proteases, lipases, pectinases, cellulases, hemicellulases, pentosanases, xylanases, and phytases, pigments, oligopeptides, dipeptides, and amino acids, and mixtures thereof.

IV. Processing Method

IVa. Nanospheres

The encapsulated flavors, and active ingredients in the nanospheres of the present invention can be prepared by the steps of (1) heating hydrophobic materials to a temperature above the melting point to form a melt, (2) dissolving or dispersing the first said flavor, and first said active ingredients in the melt, (4) emulsifying the melt in the aqueous phase; and (5) cooling the dispersion to ambient temper to form a fine suspension.

The flavors, other active ingredients can be incorporated into the hydrophobic solid nanospheres. Preferably, about 1% to about 80% of and more preferably about 1% to about 60% by weight of the active ingredients are used in forming the nanospheres.

IVb. Microspheres

The controlled release system of the present invention can be prepared by the steps of (a) incorporating the selected flavors, and active ingredients into the hydrophobic interior of the nanospheres, (b) forming an aqueous mixture comprising one or more flavor, and active agents, the nanospheres, and a water sensitive material, and (c) spray drying the mixture of the present invention to form a dry powder composition. Accordingly, the nanospheres can be encapsulated into the microsphere structure. One or more of the flavors, or active ingredients, which can be the same or different than the, flavors, and active ingredients incorporated in the nanosphere can be incorporated into the microsphere structure.

A process for producing the multi component controlled release system can include the following steps:

(i) heating hydrophobic materials to a temperature above the melting point of the materials to form a melt;
(ii) dissolving or dispersing the first said flavor into the melt;
(iii) dissolving or dispersing the first said active ingredients into the melt;
(iv) dissolving or dispersing a second said flavor, second said active ingredients, and moisture sensitive and or bioadhesive materials, such as, starch derivatives, natural gums, polyvinyl alcohol, proteins, hydrocolloids, or mixture of thereof, in the aqueous phase;

(v) heating the composition to above the melting temperature of the hydrophobic materials;

(vi) mixing the hot melt with the aqueous phase to form a dispersion;

(vii) high shear homogenization of the dispersion at a temperature above the melting temperature until a homogeneous fine dispersion is obtained having a sphere size of from about 1 micron to about 2 microns;

(viii) cooling the dispersion to ambient temperature; and (ix) spray drying the emulsified mixed suspension to form a dry powder composition.

Homogenization can be accomplished in any suitable fashion with a variety of mixers known in the art such as simple paddle or ribbon mixers although other mixers, such as ribbon or plow blenders, drum agglomerators, and high shear mixers may be used. Suitable equipment for this process include a model Rannie 100 lab homogenizer available from APV Gaulin Inc. Everett, Mass., a rotor stator high shear mixer available from Silverson Machines, of East Long Meadow, Mass., or Scott Processing Equipment Corp. of Sparta, N.J., and other high sear mixers.

The suspension is spray dried to remove the excess water. Spray drying is well known in the art and been used commercially in many applications, including foods where the core material is a flavoring oil and cosmetics where the core material is a fragrance oil. Cf. Balassa, "Microencapsulation in the Food Industry", CRC Critical Review Journal in Food Technology, July 1971, pp 245–265; Barreto, "Spray Dried Perfumes for Specialties, Soap and Chemical Specialties", December 1966; Maleeny, Spray Dried Perfumes, Soap and San Chem, January 1958, pp. 135 et seq.; Flinn and Nack, "Advances in Microencapsulation Techniques", Batelle Technical Review, Vo. 16, No. 2, pp. 2–8 (1967); U.S. Pat. Nos. 5,525,367 and 5,417,153 which are incorporated herein as references.

In the preferred embodiment, the active agent is present at a level from about 0.01% to about 60%, preferably from about 1% to about 50% by weight of the microsphere. In the preferred embodiment, the nanospheres are generally present in the water sensitive matrix at a level from about 1% to about 80%, preferably from about 1% to about 60% by weight of the matrix material with the balance being the fragrances, flavors, other active ingredients, and the water sensitive materials. In the preferred embodiment, the moisture sensitive matrix is generally present at a level from about 1% to about 80%, preferably from about 1% to about 60% by weight of the matrix material with the balance being the fragrances, flavors, other active ingredients, and the hydrophobic materials.

In one embodiment microspheres are formed by mixing nanospheres incorporating a selected active agent with polyvinyl alcohol, or compositions of polyvinyl alcohol and polysaccharides, under conditions sufficient to encapsulate the nanospheres. Preferably mixing a selected active agent with the polyvinyl alcohol, or compositions of polyvinyl alcohol and polysaccharides, until the emulsion is formed and then spray drying the emulsion to thereby form an encapsulated nanosphere. In the preferred embodiment, the moisture sensitive matrix is formed of a polyvinyl alcohol material at a level from about 1% to about 80%, preferably from about 1% to about 70% by weight of the matrix material with the balance being the amount by weight of active agents and an optimal amount of polysaccharides. In an alternate embodiment, polyvinyl alcohol is present in the matrix material in an amount of about 1% to about 80% and the weight of the polysaccharides are present in the amount of about 1% to about 80%. In the preferred embodiment, the active agent composition is generally present at a level from about 0.01% to about 80% preferably from about 1% to about 50% by weight of the encapsulated active agent with the balance being the polyvinyl alcohol or polyvinyl alcohol and polysaccharides. Optionally other conventional ingredients known in the art such as preservatives, surfactants, can be used in accordance with the teachings of the present invention. The multi-component spheres of the present invention preferably have size of from about 0.5 micron to about 300 microns, more preferably from about 1 micron to about 200 microns, most preferably from about 2 microns to about 50 microns. The present invention preferably has minimal active agents on the surface of the spheres, preferably less than 1%.

Polyvinyl alcohol is an excellent barrier material to the permeation of the volatile fragrance ingredients, and as a result the controlled release systems of the present invention do not provide perceptible odor in the dry state. Upon wetting by a sufficient amount of aqueous fluid such as a perspiration, or wetting the lips, the matrix can either dissolve to provide a burst of the active ingredients, or swell and soften the matrix to slowly release the encapsulated active agents over an extended period of time, depending on the composition of the matrix, such as the ratio of polyvinyl alcohol to other matrix materials. The use of moisture activated spheres which provide varying rates of diffusion are contemplated. For example, the moisture activated spheres may diffuse at any of the rates of the following:

(i) at steady-state or zero-order release rate in which there is a substantially continuous release per unit of time;

(ii) a first-order release rate in which the rate of release declines towards zero with time; and (iii) a delayed release in which the initial rate is slow, but then increases with time.

It has been found that a greater amount of polyvinyl alcohol in the matrix provides slower release rate as compared to a matrix including a lesser amount of polyvinyl alcohol in combination with a polysaccharide. For example, a matrix having about 70% to about 80% polyvinyl alcohol has a slower release rate than a matrix having about 30% to about 40% polysaccharide and about 40% to about 50% polyvinyl alcohol. For example, if a high amount of polyvinyl alcohol is used in the matrix, such as in the range of about 70% to about 80%, the matrix provides controlled release of the active agent over an extended period of time from the time the matrix contacts moisture up to forty-eight hours. If polyvinyl alcohol is combined with polysaccharide in the matrix, such as in the amount of 30% to about 40% polyvinyl alcohol and 30% to about 40% of polysaccharide, a greater amount of active agent is released upon contract with moisture to provide a "burst" of the active agent and the active agent is released over a shorter period of time for example from the time the matrix contacts the fluid up to the range of about 6 hours to about twenty-four hours. Typically, the active agent at the surface of the sphere can be released upon contact with the fluid with the remainder of the active agent being either released in a burst if the matrix dissolves or over an extended period of time upon swelling and softening of the matrix.

Nanospheres formed of a hydrophobic material provide a controlled release system in order to release the active agent over an extended period of time by molecular diffusion. Fragrances, flavors, and other active agents in the hydrophobic matrix of the nanospheres can be released by transient diffusion. The theoretical early and late time approximation of the release rate of the active ingredients dissolved in the hydrophobic matrix of the nanospheres can be calculated from the following equations:

Early Time Approximation
($m_t/m_{sec}$)<0.4

$$\frac{M_t}{M_\infty} = 4\left(\frac{D_p t}{\Pi r^2}\right)^{1/2} - \frac{D_p t}{r^2} \quad (1)$$

$$\frac{dM_t/M_\infty}{dt} = 2\left(\frac{D_p}{\Pi r^2 t}\right)^{1/2} - \frac{D_p}{r^2} \quad (2)$$

Late Time Approximation
($m_t/m_\infty$)>0.6

$$\frac{M_t}{M_\infty} = 1 - \frac{4}{(2.405)^2}\exp\left(\frac{-(2.405)^2 D_p t}{r^2}\right) \quad (3)$$

$$\frac{dM_t/M_\infty}{dt} = 1 - \frac{4D_p}{r^2}\exp\left(\frac{-(2.405)^2 D_p t}{r^2}\right) \quad (4)$$

wherein:
r is the radius of the cylinder,
$m_\infty$ is the amount fragrance released from the controlled release system after infinite time;
$m_t$ is the amount fragrance released from the controlled release system after time t; and
$D_p$ is the diffusion coefficient of the fragrance or aroma chemical in the matrix.

The release rate for releasing the flavor, or other active agents from the hydrophobic nanospheres is typically slower than the release rate for releasing active agent from the moisture sensitive matrix. The active agents can be incorporated into either the hydrophobic nanospheres or the moisture sensitive matrix depending on the desired time for release of the active agents. For example, a predetermined first active agent can be incorporated in the moisture sensitive matrix to be released upon product consumption and a predetermined second active agent can be incorporated in the hydrophobic nanospheres for release over an extended period of time during or after the first agent has been released. For example, the moisture sensitive matrix formed in accordance with the present invention can release the first active agent upon contact with moisture to provide a "burst" with continued release of the first active agent and nanospheres formed in accordance with the present invention can release the active agent depending on the release rate from an initial time such as within few hours, up to a period of few days.

V. Bioadhesion Measurements

Figure 2:
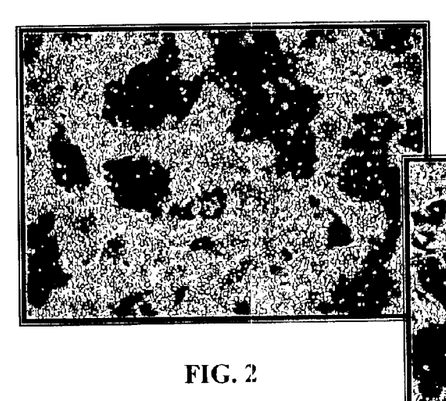
FIG. 2 is an image showing bioadhesive nanospheres to HeLa cultured cells.
Figure 3:
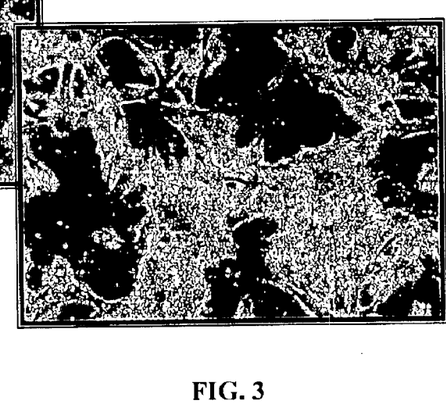
FIG. 3 is an image showing bioadhesive nanospheres of examples 1–4 to HeLa cultured cells.

The oral cavity is lined by non-keratinized, stratified, squamous epithelial cells. These types of epithelial cells also lines other soft tissue surfaces that include esophagus, vagina and cervix. A HeLa cell line that has been used to determine the ability of the nanospheres to adhere and reside in the oral cavity is an epithelial-like cell line, originally derived from a carcinoma of the cervix. HeLa cells are cultured in Minimal Essential Medium (Eagles) with 10% fetal bovine serum. To test the adherence of nanospheres to the cell surface, HeLa cells are being plated at a density of $2\times10^5$ cells per dish (35 mm) in 2 ml medium. Three dishes are seeded for each data point. On the following day, the nanospheres are being dispersed in 1 ml medium. The medium in which the cells are cultured is aspirated and replaced immediately with the nanospheres-containing medium. The nanospheres are left to adhere to the cells by gravity for time periods such as 5 minutes, 15 minutes, and 30 minutes. At each time point the medium is aspirated, and the cells surface are gently rinsed twice with 2 ml medium, simulating rise of the mouth by saliva or rinsing the mouth with water following brush. Cells are imaged immediately using an Olympus IX-70 inverted fluorescent microscope and Princeton Instruments Micromax cooled CCD camera. The images are saved and stored and analyzed using the IPLab Scientific Imaging Software (Scanalytics, Inc, VA) to determine the number of particles adherent to the cells per field. Images from three random fields are collected from each dish. Each experiment generates a total of nine data points, for each time point. The nine data points are averaged. Each experiment is repeated at least 3 times. Results obtained from three or more independent experiments are averaged and expressed as a mean±standard deviation (SD). The data are subjected to statistical analysis using the StatView program using Student's t-test method to determine whether the difference among groups is statistically significant. Results are accepted as significant when $p<0.05$. The ability of the nanospheres of the present invention to adhere to HeLa cultured cells is shown in FIG. 2. FIG. 3 shows specific adhesion of nanospheres described in examples 1 to 4 to HeLa cells.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

Preparation of Dual Flavor Controlled Release System

EXAMPLE 1

The following procedure is used for the preparation of a controlled release system that provides flavor transition as well as delivers vitamin E for extended period of time. A peppermint flavor and vitamin E are encapsulated in the hydrophobic nanospheres and a fruity flavor is encapsulated in the water sensitive microsphere. The nanospheres hydrophobic matrix is candelilla wax, commercially available from Strahl & Pitsch Inc. of West Babylon, N.Y. The microsphere water sensitive matrix is Hi-Cap™ 100 (commercially available from the National Starch and Chemical Company of Bridgewater, N.J.).

100 grams of candelilla wax is placed in an oven at 80° C. and allowed to melt. 1500 grams of deionized water are placed into 1 gallon vessel, fitted with an all-purpose silicon rubber heater (Cole-Palmer Instrument Company). 500 grams of Hi-Cap™ 100 (commercially available from the National Starch and Chemical Company of Bridgewater, N.J.) was added to the water and the aqueous solution is heated to 90° C. while mixing it with a propeller mixer. The candelilla wax is removed from the oven and 50 grams of peppermint flavor (commercially available from Noville Inc. of South-Hackensack, N.J.) and 50 grams of vitamin E (commercially available from JEEN International Corporation of Little Fall, N.J.) are mixed into the melt by hand with a glass rod. The flavor/vitamin E/wax mixture is poured into the aqueous solution and the dispersion and 300 grams of a fruity flavor (commercially available from Noville Inc. of South-Hackensack, N.J.) are homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 5% peppermint flavor and 5% vitamin E encapsulated in the solid hydrophobic nanospheres. The controlled release system obtained contains 5% peppermint flavor, 5% vitamin E, 10% candelilla wax, 30% fruity flavor, and 50% water sensitive material.

EXAMPLE 2

The following procedure is used for the preparation of a controlled release system that provides flavor transition as well as releases a cooling agent for extended period of time. A cooling agent (WS-3 commercially available from Millennium Specialty Chemicals, of Jacksonville, Fla.) is encapsulated in the hydrophobic nanospheres and a fruity flavor (commercially available from Noville Inc. of South-Hackensack, N.J.) is encapsulated in the water sensitive microsphere. The nanospheres hydrophobic matrix is candelilla wax, commercially available from Strahl & Pitsch Inc. of West Babylon, N.Y. The microsphere water sensitive matrix is Hi-Cap™ 100 (commercially available from the National Starch and Chemical Company of Bridgewater, N.J.). 150 grams of candelilla wax is placed in an oven at 80° C. and allowed to melt. 1500 grams of deionized water are placed into 1 gallon vessel, fitted with an all-purpose silicon rubber heater (Cole-Palmer Instrument Company). 450 grams of Hi-Cap™ 100 (commercially available from the National Starch and Chemical Company of Bridgewater, N.J.) was added to the water and the aqueous solution is heated to 90 degree C. while mixing it with a propeller mixer. The candelilla wax is removed from the oven and 100 grams of cooling agent (WS-3 commercially available from Millennium Specialty Chemicals, of Jacksonville, Fla.) is mixed into the melt by hand with a glass rod. The cooling agent/wax mixture is poured into the aqueous solution and the dispersion and 300 grams of a fruity flavor (commercially available from Noville Inc. of South-Hackensack, N.J.) are homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 10% Cooling agent encapsulated in the solid hydrophobic nanospheres. The controlled release system obtained contains 10% cooling agent, 15% candelilla wax, 30% fruity flavor, and 45% water sensitive material.

EXAMPLE 3

The following procedure is used for the preparation of a controlled release system that protect citral against oxidation and provides long lasting citrus mouth feel for extended period of time, by encapsulating citral in the hydrophobic nanospheres. The nanospheres hydrophobic matrix is carnauba wax, commercially available from Strahl & Pitsch Inc. of West Babylon, N.Y. The microsphere water sensitive matrix is Hi-Cap™ 100 (commercially available from the National Starch and Chemical Company of Bridgewater, N.J.).

250 grams of carnauba wax (commercially available from Strahl & Pitsch Inc. of West Babylon, N.Y.) and 50 grams of polysorbate 80 (commercially available under the trade name T-MAZ® 80K from BASF of Mt. Olive, N.J.) are placed in an oven at 90° C. and allowed to melt. 1800 grams of deionized water are placed into 1 gallon vessel, fitted with an all-purpose silicon rubber heater (Cole-Palmer Instrument Company). 500 grams of Hi-Cap™ 100 (commercially available from the National Starch and Chemical Company of Bridgewater, N.J.) was added to the water and the aqueous solution is heated to 90 degree C. while mixing it with a propeller mixer. The melt is removed from the oven and 200 grams of citral (commercially available from Noville Inc. of South-Hackensack, N.J.) are mixed into the melt by hand with a glass rod. The ciral/carnauba/polysorbate 80 mixture is poured into the aqueous solution and the dispersion and homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 20% citral encapsulated in the solid hydrophobic nanospheres. The controlled release system obtained contains 20% citral.

EXAMPLE 4

The following procedure is used for the preparation of a multi component controlled release system comprising menthol as sensory marker and cetylpyridinium chloride (CPC) as both the biologically active ingredient and bioadhesive/mucoadhesive surfactant. The solid hydrophobic nano particles are composed of candelilla wax from Strahl & Pitsch Inc. of West Babylon, N.Y.

300 grams of candelilla wax are placed in an oven at 80° C. and allowed to melt. 1600 grams of deionized water are placed into 1 Gallon vessel, fitted with an all-purpose silicon rubber heater (Cole-Palmer Instrument Company). 495 grams of Capsul Starch (commercially available from the National Starch and Chemical Company of Bridgewater, N.J.) and 5 grams of CPC are added to the water and the aqueous solution is heated to 90° C. while mixing it with a propeller mixer. The candelilla wax melt is removed from the oven and 200 grams of menthol are mixed into the wax by hand with a glass rod. The menthol/wax mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 20% menthol encapsulated in the solid hydrophobic nano particles and 0.05% CPC in the water sensitive matrix of the micro particles.

The shape and size of the nano-particles was verified by examining the samples under a scanning electron microscope (SEM). SEM studies showed that the nano-particles of Example I were spherical in nature with an average particle size of approximately 1 micron. The nanospheres were subjected to in vitro bioadhesion measurements, utilizing the technique previously described. Measurements of the adhesion of particles to cells were carried out on the nanospheres, along with the appropriate controls, using cultured human epithelial HeLa cells as a model system as described previously. The nanospheres were observed to exhibit excellent bioadhesive properties the cultured cells HeLa cells.

The nanospheres of Examples 1–4, exhibit excellent bioadhesive properties and the ability to sustain the release of the sensory marker and other active ingredients over extended period of time, when used in beverages, food products, as well as oral hygiene preparation (in accordance with the use of U.S. Pat. No. 5,882,630, issued on Mar. 16, 1999, entitled "Dentifrices Composition", incorporated by reference herein).

EXAMPLE 5

Use of Toothpaste 10 grams of the suspension of Examples I to III is admixed with 90 grams of a toothpaste composition, as described in U.S. Pat. No. 5,882,630, issued on Mar. 16, 1999, entitled "Dentifrices Composition", incorporated by reference herein and containing:

| INGREDIENT | % w/w |
| --- | --- |
| CARBOPOL 974P | 1.00 |
| THICKENING SILICA | 6.50 |
| ABRASIVE SILICA | 14.00 |
| SODIUM FLUORIDE | 0.23 |
| TITANIUM DIOXIDE | 1.00 |
| ADINOL CT 95 | 2.00 |
| SACCHARIN | 0.33 |
| POLYETHYLENE GLYCOL (400) | 17.50 |
| GLYCERIN | qs |

A toothpaste comprising 1% of the neat menthol and another sample comprising the multi component delivery system of the present invention described in Example 4 are applied to the teeth by brushing the teeth with 1 gram of the toothpaste followed by rinsing the teeth with 50 ml. of water two times.

Flavor perception in the mouth following the application of the product consisting of the nanospheres vs. the same product consisting of an equivalent amount of neat flavor, was evaluated organoleptically. A panel test is conducted to determine which product provides the strongest perception of flavor (using a scale of 0–10), after 10 minutes, 1 hour, and 3 hours following application of the product

| Flavor Intensity (a scale of 1–10) | | | |
| --- | --- | --- | --- |
| | 10 minutes | 1 Hour | 3 Hours |
| Toothpaste with neat menthol | 3 | 1 | 1 |
| Toothpaste with menthol of Example 4 | 7 | 5 | 3 |

The toothpaste containing the multi component controlled release system if the present invention provided a higher perception of menthol for an extended period of time, compared to the sample containing the neat menthol. It was readily apparent that the toothpaste containing the inventive multi component system has superior characteristics and provided longer lasting menthol perception.

Incorporation of the Controlled Release System in Chocolate Products

EXAMPLE 6

Figure 4:
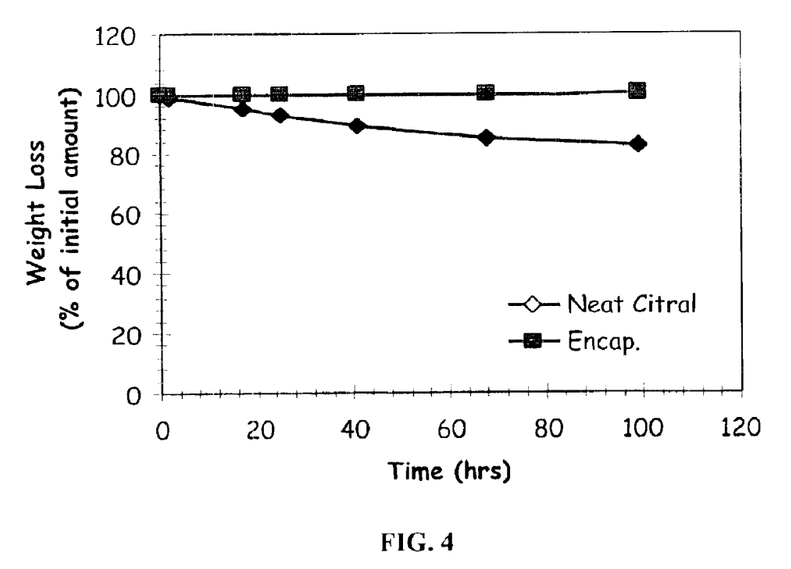
FIG. 4 is a graph of the percent weight loss of citral from the chocolate comprising the neat citral oil vs. the percent weight loss of citral from the chocolate comprising encapsulated citral in the controlled release system of the present invention.

The controlled release system described in Example 3 was incorporated in a commercial Nestle® baking chocolate. The same level of neat citral oil was also incorporated in a commercial Nestle® baking chocolate. The ability of the delivery system of the present invention to protect citral from oxidation and sustain its release was determined by weight loss measurements at 30 degrees C., as are shown in FIG. 4.

The results clearly show that during the first 100 hours we lost about 20% of the citral from the chocolate comprising the neat oil, whereas no citral was lost from the chocolate comprising the encapsulated citral in the controlled release system of the present invention.

EXAMPLE 7

The controlled release system described in Examples 1 and 2 were incorporated in a commercial Nestle® baking chocolate. The ability of chocolate comprising controlled release system of Example 1 and 2 to yield a high impact flavor "burst" upon eating the chocolate, provide flavor transition, and prolong flavor perception in the mouth over an extended period of time was evaluated.

The chocolate bars were tested and flavor character as well as flavor intensity is evaluated. Flavor transition was clearly noticed a minute after testing the chocolate. The cooling sensation of the chocolate comprising the delivery system of example 2 was sensed for 3 hours after consumption of the product.

Incorporation of the Controlled Release System in Powder Drink

EXAMPLE 8

The performance of a powder drink comprising the controlled release system of Example 3 (i.e., the ability to yield long lasting citrus mouth feel over extended period of time) was evaluated and compared to the performance of the same product comprising the neat citral, at the same level.

Flavor perception in the mouth following the use of the above drinks comprising the nanospheres vs. the same drink comprising an equivalent amount of neat flavor, was evaluated organoleptically. A panel test is conducted to determine which product provides the strongest perception of flavor (using a scale of 0–10), after 1 minutes, 10 minutes, and 20 minutes following consumption of the product

| Flavor Intensity (a scale of 1–10) | | | |
| --- | --- | --- | --- |
| | 1 minutes | 10 minutes | 30 minutes |
| Drink with neat citral | 4 | 2 | 1 |
| Drink with citral of Example 3 | 8 | 6 | 4 |

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. A food product comprising a plurality of solid nanospheres formed of a hydrophobic material, said hydrophobic material is selected from the group consisting of carnauba wax, candelilla wax, and mixtures thereof, each of said solid hydrophobic nanospheres encapsulated an effective amount of a first active agent contained therein, said plurality of nanospheres being homogenously dispersed within a moisture sensitive microsphere, said microsphere is formed of a moisture sensitive matrix material, said moisture-sensitive matrix material is selected from the group consisting of water soluble synthetic polymers, water dispersible synthetic polymer, starch derivative, natural gum, polysaccharide, protein, hydrocolloid and mixtures thereof, wherein said microsphere dissolves upon contact with said moisture to provide a burst of said nanospheres or said microsphere swells or softens to slowly release said nanospheres and said nanospheres release said active agent continuously thereafter for an extended period of time.

2. The food product of claim 1 wherein said hydrophobic material has a melting point between 30° C. and 90° C.

3. The food product of claim 1 wherein said moisture sensitive matrix material releases said active agent upon contact with moisture and continuously thereafter for an extended period of time.

4. The food product of claim 1 wherein said water-soluble synthetic polymer is selected from the group consisting of: polyvinyl pyrrolidone, water soluble cellulose, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide and polyester and mixtures thereof.

5. The food product of claim 1 wherein said natural gum is gum arabic.

6. The food product of claim 1 wherein said nanospheres further comprises a surfactant.

7. The food product of claim 1 further comprising a bioadhesive material surrounding said solid hydrophobic nano-spheres or a bioadhesive material within said moisture sensitive matrix material, wherein said bioadhesive material is selected from the group consisting of bioerodible hydrogels, polyhyaluronic acid, casein, gelatin, glutin, polyanhydride, polyacrylic acid, alginate, chitosan, poly (methyl methacrylate), poly(ethyl methacrylate), poly (butyl methacrylate), poly(isobutyl methacrylate), poly(hexl methacrylate), poly(isodecl methacrylate), poly(lauryl methacrylate), poly(phenyl methacrylate), poly(methyl acrylate), poly(isopropyl acrylate), poly(isobutyl acrylate), and poly(octadecl acrylate), poly(fumaric-co-sebacic)acid and mixtures thereof.

8. The food product of claim 1 further comprising a bioadhesive material surrounding said solid hydrophobic nanospheres or a bioadhesive material within said moisture sensitive matrix material, wherein said bioadhesive material is a polymer comprising anhydride monomers or oligomers.

9. The food product of claim 1 further comprising one or more of an amphoteric surfactant, non-ionic surfactant and cationic surfactant.

10. The food product of claim 1 wherein said moisture sensitive matrix comprises a second active agent, said second active agent being the same or different as said first active agent, said moisture sensitive matrix material releases said second active agent upon contact with moisture and continuously thereafter for an extended period of time.

11. The food product of claim 10 wherein said moisture sensitive microsphere releases an effective amount of said second active agent to provide a burst of said active agent.

12. The food product of claim 11 wherein after said burst of said second active agent, said second active agent is continuously released for an extended period of time.

13. A food product of claim 10 wherein said first active agent and said second active agent are selected from one or more of a flavorant, sensory marker, or nutraceutical.

14. The food product of claim 13 wherein said second active agent flavorant is selected from the group consisting of: crystalline ingredients, dairy ingredients, spices, natural flavors, artificial flavors, thickening agents, protein compounds, vegetable gums and combinations thereof.

15. The food product of claim 10 wherein said second active agent is a first flavor and said first active agent is a second flavor, said first flavor being different than said second flavor wherein release of said first flavor and said second flavor provides an organoleptic perception of a flavor transition.

16. The food product of claim 13 wherein said second active agent is a nutraceutical is selected from the group consisting of: antioxidants, phytochemicals, hormones, vitamins, Vitamin A, Vitamin B1, Vitamin B2, Vitamin B6, Vitamin B12, Vitamin C, Vitamin D, Vitamin E, Vitamin K, pantothenate, folic acid, pro-vitamins, minerals, calcium, selenium, magnesium salts, iron, iron salts, microorganisms, bacteria, lactobacilli, fungi, yeast, prebiotics, probiotics, unsaturated fatty acids, omega-3 fatty acids, mid-chain triglycerides, nutritional supplements, enzymes, amylases, proteases, lipases, pectinases, cellulases, hemicellulases, pentosanases, xylanases, and phytases, pigments, oligopeptides, dipeptides, amino acids and mixtures thereof.

17. The food product of claim 13 wherein said second active agent is a sensory marker of a flavor or cooling agent.

18. The food product of claim 17 wherein said cooling agent is selected from the group consisting of: menthol, non-volatile menthol analogs, menthyl lactate, menthyl ethoxyacetate, menthone glycerinacetal, 3-1-menthoxypropane-1,2-diol, ethyl 1-menthyl carbonate, (1S, 3S,4R)-p-menth-8-en-3-ol, menthyl pyrrolidone carboxylate, N-substituted-p-menthane-3-carboxamide, N-ethyl-p-menthane-3-carboxamide, N,2,3-trimethyl-2-isopropylbutanamide, ketal coolants, 1-menthon-1d-isomenthon glycerin ketal, 3-1-menthoxypropane-1,2-diol, N-ethyl-p-menthane-3-carboxamide, N,2,3-trimethyl-2-isopropylbutanamide, menthyl lactate, menthone glycerinacetal and menthyl ethoxyacetate.

19. The food product of claim 1 wherein said nanospheres have an average particle diameter between about 0.01 microns and about 10 microns.

20. The food product of claim 1 wherein said first active agent comprises a flavorant, sensory marker or nutraceutical.

21. The food product of claim 20 wherein said flavorant is selected from the group consisting of: crystalline ingredients, dairy ingredients, spices, natural flavors, artificial flavors, thickening agents, protein compounds, vegetable gums and combinations thereof.

22. The food product of claim 20 wherein said nutraceutical is selected from the group consisting of: antioxidants, phytochemicals, hormones, vitamins, Vitamin A, Vitamin B1, Vitamin B2, Vitamin B6, Vitamin B12, Vitamin C, Vitamin D, Vitamin E, Vitamin K, pantothenate, folic acid, pro-vitamins, minerals, calcium, selenium, magnesium salts, iron, iron salts, microorganisms, bacteria, lactobacilli, fungi, yeast, prebiotics, probiotics, unsaturated fatty acids, omega-3 fatty acids, mid-chain triglycerides, nutritional supplements, enzymes, amylases, proteases, lipases, pectinases, cellulases, hemicellulases, pentosanases, xylanases, and phytases, pigments, oligopeptides, dipeptides, amino acids and mixtures thereof.

23. The food product of claim 20 wherein said sensory marker is a cooling agent is selected from the group consisting of: menthol, non-volatile menthol analogs, menthyl lactate, menthyl ethoxyacetate, menthone glycerinacetal, 3-1-menthoxypropane-1,2-diol, ethyl 1-menthyl carbonate, (1S,3S,4R)-p-menth-8-en-3-ol, menthyl pyrrolidone carboxylate, N-substituted-p-menthane-3-carboxamide, N-ethyl-p-menthane-3-carboxamide, N,2,3-trimethyl-2-isopropylbutanamide, ketal coolants, 1-menthon-1d-isomenthon glycerin ketal, 3-1-menthoxypropane-1,2-diol, N-ethyl-p-menthane-3-carboxamide, N,2,3-trimethyl-2-isopropylbutanamide, menthyl lactate, menthone glycerinacetal and menthyl ethoxyacetate.

24. A hydrated sauce or soup composition comprising a plurality of solid nanospheres formed of a hydrophobic material, said hydrophobic material is selected from the group consisting of carnauba wax, candelilla wax, and mixtures thereof, each of said solid hydrophobic nanospheres encapsulated an effective amount of a first active agent contained therein, said plurality of nanospheres being homogenously dispersed within a moisture sensitive microsphere, said microsphere is formed of a moisture sensitive matrix material, said moisture-sensitive matrix material is selected from the group consisting of water soluble synthetic polymers, water dispersible synthetic polymer, starch derivative, natural gum, polysaccharide, protein, hydrocolloid and mixtures thereof, wherein said microsphere dissolves upon contact with said moisture to provide a burst of said nanospheres or said microsphere swells or softens to slowly release said nanospheres and said nanospheres release said active agent continuously thereafter for an extended period of time.

25. The hydratable sauce or soup composition of claim 24 wherein said first active agent comprises a flavorant, sensory marker or nutraceutical.

26. The hydratable sauce or soup composition of claim 25 wherein said flavorant is selected from the group consisting of: crystalline ingredients, dairy ingredients, natural flavors, artificial flavors, thickening agents, protein compounds, vegetable gums and combinations thereof.

27. The hydratable sauce or soup composition of claim 25 wherein said nutraceutical is selected from the group consisting of: antioxidants, phytochemicals, hormones, vitamins, Vitamin A, Vitamin B1, Vitamin B2, Vitamin B6, Vitamin B12, Vitamin C, Vitamin D, Vitamin E, Vitamin K, pantothenate, folic acid, pro-vitamins, minerals, calcium, selenium, magnesium salts, iron, iron salts, microorganisms, bacteria, lactobacilli, fungi, yeast, prebiotics, probiotics, unsaturated fatty acids, omega-3 fatty acids, mid-chain triglycerides, nutritional supplements, enzymes, amylases, proteases, lipases, pectinases, cellulases, hemicellulases, pentosanases, xylanases, and phytases, pigments, oligopeptides, dipeptides, amino acids and mixtures thereof.

28. The hydratable sauce or soup of claim 24 wherein said moisture sensitive matrix comprises a second active agent, said second active agent being the same or different as said first active agent, said moisture sensitive matrix material releases said second active agent upon contact with moisture and continuously thereafter for an extended period of time, said first active agent and said second active agent are selected from one or more of a flavorant, sensory marker, or nutraceutical.

29. The hydratable sauce or soup of claim 28 wherein said flavorant is selected from the group consisting of: crystalline ingredients, dairy ingredients, spices, natural flavors, artificial flavors, thickening agents, protein compounds, vegetable gums and combinations thereof.

30. The hydratable sauce or soup of claim 28 wherein said nutraceutical comprises a nutraceutical component selected from the group consisting of: antioxidants, phytochemicals, hormones, vitamins, Vitamin A, Vitamin B1, Vitamin B2, Vitamin B6, Vitamin B12, Vitamin C, Vitamin D, Vitamin E, Vitamin K, pantothenate, folic acid, pro-vitamins, minerals, calcium, selenium, magnesium salts, iron, iron salts, microorganisms, bacteria, lactobacilli, fungi, yeast, prebiotics, probiotics, unsaturated fatty acids, omega-3 fatty acids, mid-chain triglycerides, nutritional supplements, enzymes, amylases, proteases, lipases, pectinases, cellulases, hemicellulases, pentosanases, xylanases, and phytases, pigments, oligopeptides, dipeptides, amino acids and mixtures thereof.

* * * * *